(12) United States Patent
Kertser

(10) Patent No.: US 11,964,106 B2
(45) Date of Patent: Apr. 23, 2024

(54) BYPASS FILTER

(71) Applicant: Oridion Medical 1987 Ltd., Jerusalem (IL)

(72) Inventor: Michael Kertser, Bney Aish (IL)

(73) Assignee: Oridion Medical 1987 Ltd., Jerusalem (IL)

(*) Notice: Subject to any disclaimer, the term of this patent is extended or adjusted under 35 U.S.C. 154(b) by 809 days.

(21) Appl. No.: 16/955,869

(22) PCT Filed: Oct. 24, 2018

(86) PCT No.: PCT/IL2018/051137
§ 371 (c)(1),
(2) Date: Jun. 19, 2020

(87) PCT Pub. No.: WO2019/123446
PCT Pub. Date: Jun. 27, 2019

(65) Prior Publication Data
US 2021/0016045 A1 Jan. 21, 2021

Related U.S. Application Data

(60) Provisional application No. 62/608,668, filed on Dec. 21, 2017.

(51) Int. Cl.
*A61M 16/10* (2006.01)
*A61M 16/00* (2006.01)
*A61M 16/08* (2006.01)

(52) U.S. Cl.
CPC .... *A61M 16/1065* (2014.02); *A61M 16/0093* (2014.02); *A61M 16/0808* (2013.01);
(Continued)

(58) Field of Classification Search
CPC ............ A61M 16/0093; A61M 16/107; A61M 16/0808; A61M 16/1065;
(Continued)

(56) References Cited

U.S. PATENT DOCUMENTS 1,584,743 A * 5/1926 Hensley ................. B01D 35/02
210/422
5,131,387 A * 7/1992 French ................... A61B 5/097
128/205.12
(Continued)

FOREIGN PATENT DOCUMENTS

WO 2003013340 A3 2/2003

OTHER PUBLICATIONS

International Application No. PCT/IL2018/051137 International Search Report and Written Opinion dated Feb. 18, 2019, 9 pages.
(Continued)

*Primary Examiner* — Colin W Stuart
*Assistant Examiner* — Douglas Y Sul
(74) *Attorney, Agent, or Firm* — Fletcher Yoder, P.C.

(57) ABSTRACT

A bypass filter comprising a conduit having a main passageway configured for passage of fluid from an upstream end of the conduit to a downstream end of the conduit; The bypass filter further comprises a main filter located within the main passageway and configured for preventing passage therethrough of a predetermined substance within the fluid, while allowing a remainder of the fluid to pass towards the downstream end of the conduit; The bypass filter has an upstream opening in the conduit located upstream of the main filter and being in fluid communication with the main passageway at an upstream end of the conduit and a downstream opening in the conduit located downstream of the main filter and being in fluid communication with the main passageway at a downstream end of the conduit; The bypass filter also comprises an auxiliary filter being in fluid communication with both the upstream opening and the downstream opening for passing the fluid between the openings while at least partially absorbing the substance.

20 Claims, 4 Drawing Sheets

(52) U.S. Cl.
CPC ...... *A61M 16/1005* (2014.02); *A61M 16/107* (2014.02); *A61M 2016/103* (2013.01); *A61M 2205/7527* (2013.01); *A61M 2205/7536* (2013.01)

(58) Field of Classification Search
CPC .. A61M 2205/7527; A61M 2205/7536; B01D 53/263; B01D 53/261; B01D 53/266; B01D 53/268; B01D 2201/02; B01D 2201/60
See application file for complete search history.

(56) References Cited

U.S. PATENT DOCUMENTS

| | | | | |
|---|---|---|---|---|
| 5,558,087 A | * | 9/1996 | Psaros | B01D 53/229 |
| | | | | 128/205.27 |
| 5,616,158 A | * | 4/1997 | Biendarra | G01N 33/497 |
| | | | | 128/205.27 |
| 5,657,750 A | * | 8/1997 | Colman | A61M 16/085 |
| | | | | 128/205.27 |
| 7,137,390 B2 | * | 11/2006 | Fudge | A61B 5/097 |
| | | | | 128/205.12 |
| 2003/0024528 A1 | | 2/2003 | Graham | |
| 2005/0166917 A1 | * | 8/2005 | Ahlmen | A61M 16/107 |
| | | | | 128/201.13 |
| 2007/0062255 A1 | | 3/2007 | Talton | |
| 2011/0237969 A1 | | 9/2011 | Eckerbom et al. | |
| 2011/0283884 A1 | * | 11/2011 | Larsen | A61M 16/085 |
| | | | | 96/417 |
| 2013/0220129 A1 | | 8/2013 | Henning et al. | |
| 2014/0058281 A1 | | 2/2014 | Larsen et al. | |

OTHER PUBLICATIONS

EP Application No. 18890588.9 Extended EP Search Report dated Aug. 3, 2021, 10 pages.

* cited by examiner

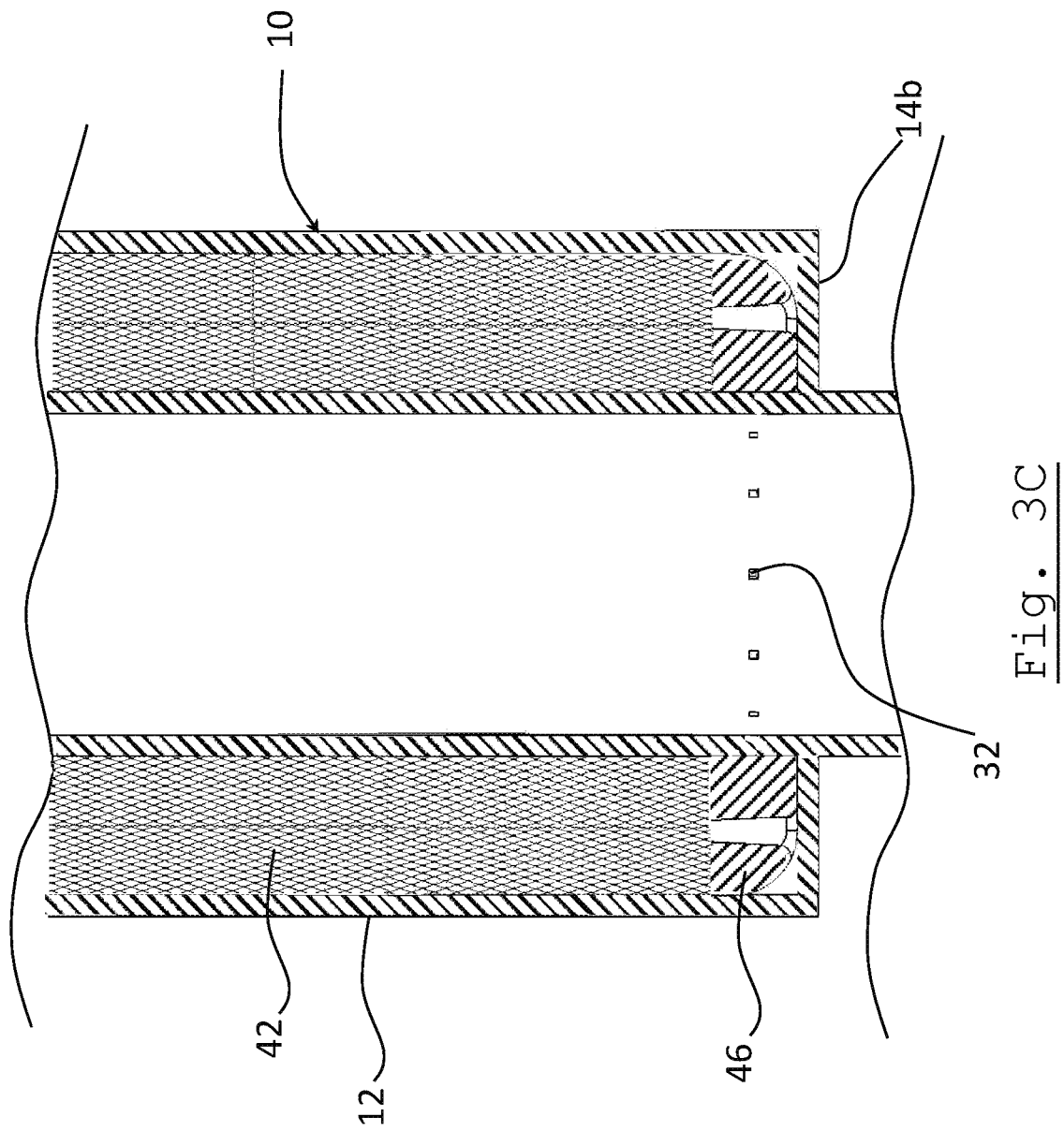

BYPASS FILTER

CROSS REFERENCE TO RELATED APPLICATIONS

This is a U.S. National Stage filing of Application No. PCT/IL2018/051137, filed on Oct. 24, 2018, which claims the benefit of U.S. Provisional Application No. 62/608,668 filed on Dec. 21, 2017, the disclosures of which are incorporated herein by reference.

TECHNOLOGICAL FIELD

The present invention is in the field of humidity filters, in particular, filters used in respiratory devices.

BACKGROUND OF THE INVENTION

In the field of capnography, it is common to obtain a $CO_2$ reading from a patient by connecting the patient to a nasal cannula. In operation, the nasal cannula is configured for receiving the exhaled air from the patient's mouth/nose whereafter this air is passed through appropriate tubing towards a downstream end and to a $CO_2$ analyzer.

Since the analyzer is configured for monitoring $CO_2$ levels, it is common to provide the tubing with a humidity filter, usually located closer to the downstream end, in order to absorb humidity and/or prevent it from passing into the analyzer.

Acknowledgement of the above references herein is not to be inferred as meaning that these are in any way relevant to the patentability of the presently disclosed subject matter.

GENERAL DESCRIPTION

In accordance with one aspect of the subject matter of the present application, there is provided a bypass filter comprising:
- a conduit having a main passageway configured for passage of fluid from an upstream end of the conduit to a downstream end of the conduit;
- a main filter located within said main passageway and configured for preventing passage therethrough of a predetermined substance within said fluid, while allowing a remainder of said fluid to pass towards the downstream end of the conduit;
- an upstream opening in said conduit located upstream of the blocking element and being in fluid communication with said main passageway at an upstream end of the conduit and a downstream opening in said conduit located downstream of the blocking element and being in fluid communication with said main passageway at a downstream end of the conduit; and
- a auxiliary filter being in fluid communication with both said upstream opening and said downstream opening for passing said fluid between the openings while at least partially absorbing said substance.

In particular, the bypass filter can be configured for allowing passage of gases through the main passageway between the upstream end and the downstream end, while preventing liquids from reaching the downstream end of the conduit. In this case the bypass filter is configured to function as a humidity filter. In accordance with a specific example, the bypass filter may be used in consumables configured for respiratory use, in which case said liquid may be water vapor (also referred herein as moisture or humidity). For the purpose of clarity, further examples and features will be referred to in connection with the above example of gases and liquid (i.e. a filter preventing passage of liquids while allowing passage of gases).

However, it should be understood that for all intents and purposes, the present invention is not restricted to liquids (or water vapor in particular) and it is the unique design of the bypass filter which allows for the henceforth described features, which may be implemented for a variety of substances.

The bypass filter is designed such that when a certain amount of water accumulates on an upstream surface of the main filter, the main passageway becomes blocked to gases, preventing passage of said gases through the main filter. The arrangement is such that once the main passageway becomes blocked, the fluid (including both gases and liquids) is diverted to travel from an upstream end of the conduit to a downstream end of the conduit via passage through the auxiliary filter, during which passage liquids become absorbed in the auxiliary filter, allowing the gases to travel to the downstream end of the conduit. In this specific example, the bypass filter is a humidity filter, the main filter can be hydrophobic while the auxiliary filter is hydrophilic.

The conduit can further comprise one or more drainage openings being in fluid communication with the auxiliary filter, and the main filter may be designed so as to guide said liquid towards said auxiliary filter via said one or more drainage openings. Guiding may be performed, for example, by the geometric shape of the main filter, where the liquid is promoted to flow towards the one or more drainage openings. In particular, the main passageway can have a cross-section and the main filter may be located within the main passageway, entirely obstructing said cross-section.

The upstream surface of the main filter may have at least one segment tapering outwards away from the upstream end and leading to said one or more drainage openings. In accordance with a particular example, the upstream surface of the main filter can have at least a partially conical geometry such that the wide end of the cone is adjacent to said one or more drainage openings, so that any water passing through the passageway and encountering the upstream surface of the main filter will simply flow down the conical surface towards the periphery of the conduit where the drainage openings are located.

In accordance with a specific embodiment, the auxiliary filter may surround the conduit, at least partially, for example, be in the form of a sleeve or sleeve portion, extending along the outer side of the conduit. Under this embodiment, the following design variations may apply:
  a) the auxiliary filter extends along the outside of the conduit such that it overlaps the upstream opening but does not overlap the downstream opening;
  b) the auxiliary filter extends along the outside of the conduit such that it overlaps the downstream opening but does not overlap the upstream opening; and
  c) the auxiliary filter extends along the outside of the conduit such that it overlaps both the upstream opening and the downstream opening.

The term 'overlaps' is used herein to denote that an inner surface of the auxiliary filter is juxtaposed with the opening.

The auxiliary filter may also be fitted with a downstream cover preventing water from dripping down after being absorbed within the filter. The downstream cover may comprise one or more apertures configured for allowing the gases to escape via the downstream end of the auxiliary filter. This arrangement allows the gases to pass through to the downstream opening of the conduit while retaining the water within the auxiliary filter.

In addition, when the auxiliary filter is designed as a sleeve, the bypass filter may further comprise an external housing surrounding at least the auxiliary filter. In accordance with a specific example, the housing may fully encapsulate the bypass filter and extending between an upstream end located upstream of the upstream opening of the conduit, and a downstream end located downstream of the downstream opening of the conduit.

The auxiliary filter may be designed such that upon absorbing the water, it increases in dimensions, e.g. swelling. In particular, in case a sufficiently rigid external housing is used, such swelling of the auxiliary filter may cause it to extend axially.

In operation, when exhaled gases mixed with water vapor enter the main passageway and advance towards the main filter, the gases pass freely through the main filter while water vapor condenses on the main filter and gradually guided to flow towards the auxiliary filter where it is absorbed. Under this mode of operation, the pressure scheme is such that the pressure difference between the upstream and downstream sides of the main filter is higher than the pressure difference between the upstream and downstream side of the auxiliary filter, whereby the gases flow through the main filter.

However, if a sufficiently large amount of water vapor or water reaches the main filter at once, e.g. a large water drop, it may cover the main filter, thereby completely blocking the main passageway. In this case, the gases can no longer flow through the main filter and pressure begins to increase on the upstream end of the main filter. Once this pressure increases sufficiently, the gases can flow through the upstream opening of the conduit, then through the auxiliary filter and eventually, exiting from a downstream end of the auxiliary filter, towards the downstream opening of the conduit.

During this process of passing through the auxiliary filter, water vapor is absorbed therein. Simultaneously, the water previously blocking the main filter is guided towards the one or more drainage openings in the conduit and is also being gradually absorbed in the auxiliary filter. As a result, the auxiliary filter expands and the pressure on the upstream side of the main filter is decreased, while the main filter is cleared of the water blocking the passageway. This balances out the pressure scheme, allowing the gases to once again flow through the main filter.

Thus, throughout the operation of the bypass filter, the auxiliary filter keeps expanding each time it absorbs an additional amount of water. In accordance with another feature of the present invention, the external housing may comprise a stopper configured for limiting the expansion of the auxiliary filter. Specifically, the stopper can be constituted by a downstream end of the external housing.

In addition, the design may be such that once the auxiliary filter expands sufficiently to reach the stopper, the downstream cover abuts the downstream end of the external housing, wherein the one or more apertures of the downstream cover become blocked, thereby preventing passage of gases to the downstream opening of the conduit. Such a design allows defining a predetermined lifespan for the bypass filter. Since the bypass filter is implemented in a consumable, it can be designed to have a predetermined lifespan according to an estimated amount of water vapor.

The above design of the bypass filter allows for constant flow of gases towards the downstream end of the conduit. Contrary to common filters, in which the gases are prevented from flowing towards the downstream end of the conduit until much of the water is absorbed in the filter, the bypass filter of the present invention allows considerably reducing this 'delay' time.

When the bypass filter is applied to respiratory devices, e.g. capnography measurements, the reduction in 'delay' time is proportionally reflected in the Rise Time on the capnographic diagram. Reducing the Rise Time, in turn, allows for a more accurate measurement of respiratory functions.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 3C is a schematic enlarged view of the downstream portion of the bypass filter shown in FIGS. 2B and 3B, shown in an end state of the bypass filter.

Figure 1:
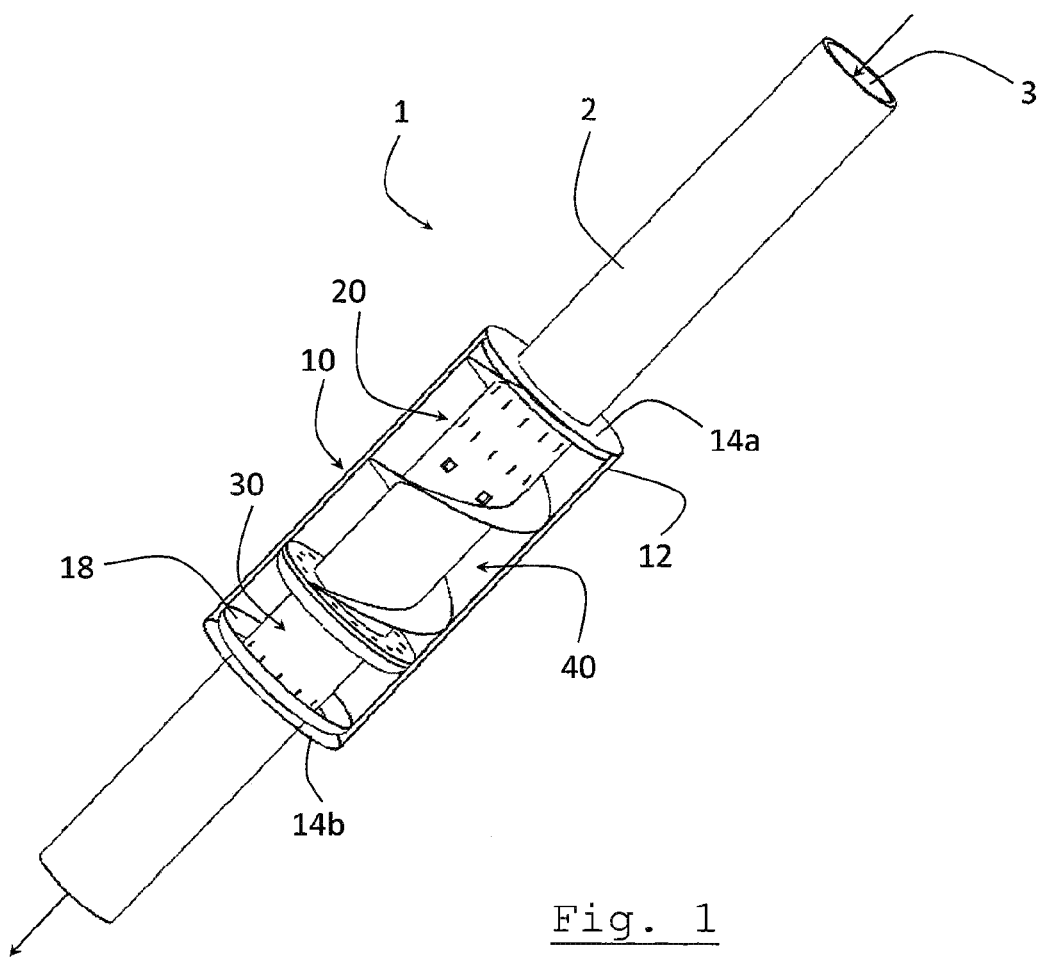
FIG. 1 is a schematic isometric view of a bypass filter according to the present application.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF EMBODIMENTS

Attention is first drawn to FIG. 1 in which the bypass filter of the present application is shown, generally designated as 1, and comprising a conduit 2 formed with a main passageway 3 and a main filter arrangement having an upstream filter portion 20 and a downstream filter portion 30, and a housing 10 surrounding a portion of the conduit 2 and comprising an auxiliary filter 40.

Figure 2A:
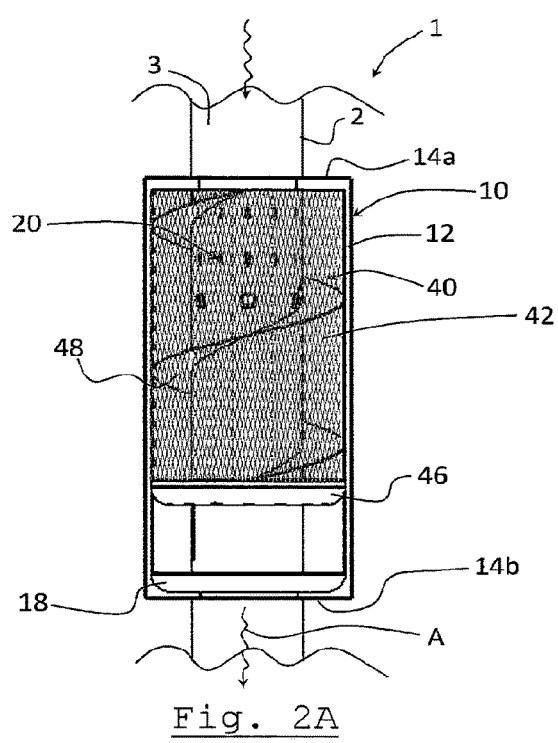
FIG. 2A is a schematic front view of the bypass filter shown in FIG. 1.
Figure 2B:
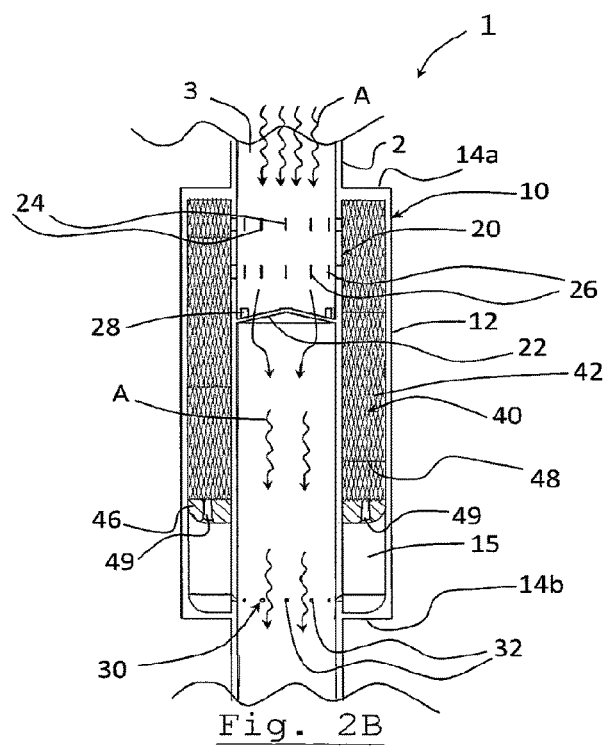
FIG. 2B is a schematic longitudinal cross-section view of the bypass filter shown in FIG. 2A.
Figure 3A:
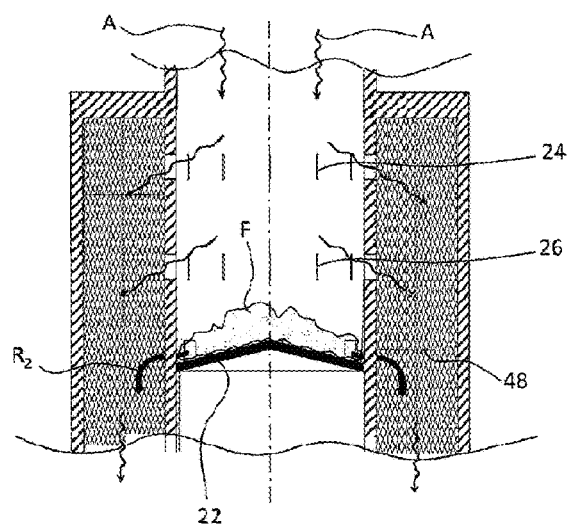
FIG. 3A is a schematic enlarged view of an upstream portion of the bypass filter shown in FIG. 2B, shown in a state where liquid enters the bypass filter.

With additional reference being made to FIGS. 2A and 2B, the upstream filter portion 20 comprises a selective filter membrane 22 configured for allowing passage of gas (e.g. air) therethrough to the downstream side of the conduit, while preventing passage of fluid (see F in FIG. 3A). In addition, the upstream filter portion 20 comprises a first set of bypass apertures 24 formed in the conduit 2 and located upstream of the selective membrane 22, and a second set of bypass apertures 26 formed in the conduit 2 and located between the first set of apertures 24 and the selective membrane 22.

Figure 3B:
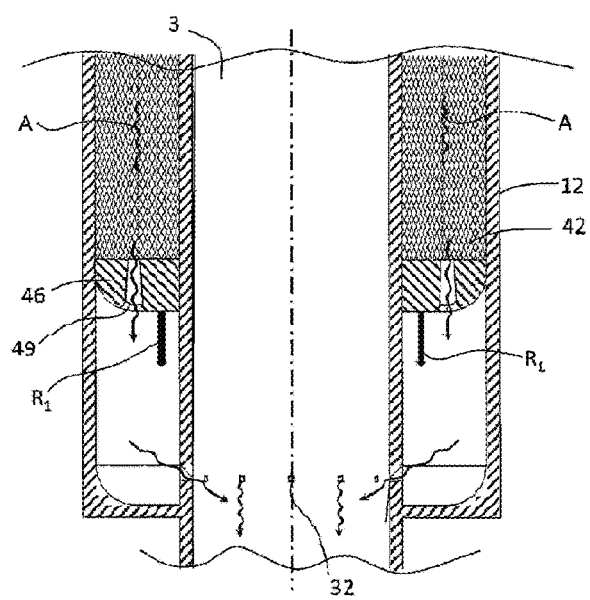
FIG. 3B is a schematic enlarged view of a downstream portion of the bypass filter shown in FIG. 2B.

The selective membrane 22 is of a conical shape tapered towards the downstream end of the conduit, such that the apex of the selective membrane 22 is located more upstream than the periphery of the selective membrane 22. The upstream filter portion further comprises a set of drainage openings 28 formed in the conduit 2 and located at the periphery of the selective membrane 22. As will be shown with respect to FIGS. 3A and 3B, the conical shape of the selective membrane 22 allows directing fluid towards the drainage openings 28.

The downstream filter portion 30 is also formed with a set of apertures 32, located downstream of the selective membrane 22.

The housing 10 surrounding the conduit 2 has a body 12 extending axially between an upstream end 14a, located upstream of the first set of apertures 24, and a downstream end 14a located downstream of the set of apertures 32 of the downstream filter portion 30. The housing 10 accommodates therein an auxiliary filter 40 comprising a main filter body 42 which extends from the upstream end 14a of the housing body 12 towards the downstream end 14b of the housing body 12. The downward end of the filter body 42 is fitted with a downstream cover 46, formed with apertures 49. It is noted that the filter body 42 does not extend all the way, leaving a space 15 defined between the downstream cover 46 and the downstream end of the housing 14b.

In addition, the filter body 42 is provided with a support spring 48 spiraling around the main conduit and configured both for supporting the shape of the filter body 42 and for allowing the filter body 42 to expand uniformly.

With particular reference being made to FIG. 2B, under a regular mode of operation of the bypass filter, when air A is passed through the main passageway 3 of the conduit 2, it progresses downwards towards the selective membrane 22, passes through it and proceeds to the downstream end of the conduit 2. Under this mode of operation, the air A does not pass into the auxiliary filter 40 via apertures 24, 26. Simultaneously, any light humidity contained within the air is absorbed within the filter body 42 via the apertures 24, 26.

Turning now to FIG. 3A, a state of the bypass filter 1 is shown in which a large amount of liquid F accumulates on the selective membrane 22. Since the selective membrane 22 does not allow passage of liquid therethrough (e.g. hydrophilic), the liquid F accumulates on the selective membrane 22 and blocks passage to the incoming air A.

As a result of the above, two processes take place simultaneously:

The air A, which is prevented from passing through the selective membrane 22 is diverted to apertures 24, 26, where it enters the filter body 42, travels therealong and is emitted via the apertures 49 in the downstream cover 46. From there, the air A proceeds towards the downstream apertures 32 where it reenters the main passageway 3 of the conduit 2, thereby bypassing the main filter.

The liquid F accumulated on the selective membrane 22 is diverted, owing to the conical shape of the selective membrane 22, to the periphery thereof towards drainage openings 28. The liquid F penetrates the filter body 42 via the drainage openings 28 and becomes absorbed therein.

Once the liquid F is sufficiently absorbed, the selective membrane 22 is unblocked, allowing air A to flow back through the membrane 22, reverting to the mode of operation shown in FIG. 2B.

It should be noted that the bypass filter is arranged such that under normal circumstances (i.e. no liquid blocking the selective membrane 22), the path of least resistance for the air A is through the selective membrane 22 rather than through the filter body 42.

In addition, as the filter body 42 absorbs liquids and humidity, it expands axially such that the downstream cover 46 displaces towards the downstream end 14b of the housing 10. With additional reference being made to FIG. 3C, the filter body 42 is shown in a state where it is fully expanded and the downstream cover 46 is flush with the downstream end 14b of the housing 10 (also referred herein as an 'end state' of the filter). In this state, the volume of space 15 is reduced nearly to zero, and the filter body 42 can no longer expand and can no longer absorb any more liquid.

Thus, in this state, if the selective membrane 22 is blocked by fluid, the fluid will no longer drain into the filter body 42. In addition, in the end state of the filter, the apertures 49 in the downstream cover 46 are flush against the downstream end 14b of the housing 10, thereby blocking passage of air to the downstream apertures 32. Thus, even if air were to travel through the filter body 42, it would not be able to escape to a downstream end of the passageway 3.

This state is considered an 'end state' or an 'end of life state' because the filter becomes unusable and it is required to replace is with a new bypass filter. The life span of the bypass filter is therefore determined by two main parameters: the initial axial length of the space 15, and the expansion rate of the filter body 42 when coming into contact with a liquid.

Those skilled in the art to which this invention pertains will readily appreciate that numerous changes, variations, and modifications can be made without departing from the scope of the invention, mutatis mutandis.

The invention claimed is:

1. A bypass filter comprising:
   a conduit comprising a conduit wall, the conduit wall defining a main passageway configured for passage of fluid from an upstream end of the conduit to a downstream end of the conduit;
   a main filter located within the main passageway and configured for preventing passage therethrough of a predetermined substance within the fluid, while allowing a remainder of the fluid to pass towards the downstream end of the conduit, wherein the main filter blocks the main passageway to gases in response to a predetermined amount of water accumulating on an upstream surface of the main filter and prevents passage of the gases through the main filter,
   wherein the conduit wall defines an upstream opening located upstream of the main filter and being in fluid communication with the main passageway at an upstream end of the conduit and a downstream opening located downstream of the main filter and being in fluid communication with the main passageway at a downstream end of the conduit; and
   an auxiliary filter extending between a first auxiliary filter end and a second auxiliary filter end, the auxiliary filter being in fluid communication with both the upstream opening and the downstream opening, wherein the auxiliary filter is configured to enable the fluid to pass between the upstream opening and the downstream opening while at least partially absorbing the substance,
   wherein the main filter is located within the main passageway at a position between the first auxiliary filter end and the second auxiliary filter end, and wherein the bypass filter diverts fluid to travel from the upstream end of the conduit to the downstream end of the conduit via passage through the auxiliary filter when the main passageway is blocked.

2. The bypass filter according to claim 1, wherein the bypass filter is configured to allow passage of gases through the main passageway between the upstream end and the downstream end, while preventing liquids from reaching the downstream end of the conduit.

3. The bypass filter according to claim 1, wherein the auxiliary filter is configured to allow the gases to travel to the downstream end of the conduit.

4. The bypass filter according to claim 1, wherein the bypass filter is a humidity filter, the main filter is hydrophobic, and the auxiliary filter is hydrophilic.

5. The bypass filter according to claim 1, wherein the conduit further comprises one or more drainage openings in fluid communication with the auxiliary filter.

6. The bypass filter according to claim 5, wherein the main filter is located within the main passageway, entirely obstructing a cross-section of the main passageway.

7. The bypass filter according to claim 5, wherein the upstream surface of the main filter has at least one segment tapering outwards away from the upstream end and leading to the one or more drainage openings.

8. The bypass filter according to claim 7, wherein the upstream surface of the main filter has at least a partially conical geometry such that a wide end of the partially conical geometry is adjacent to the one or more drainage openings.

9. The bypass filter according to claim 1, wherein the auxiliary filter at least partially surrounds the conduit.

10. The bypass filter according to claim 9, wherein the bypass filter comprises a sleeve or a sleeve portion extending along an outer side of the conduit.

11. The bypass filter according to claim 10, wherein any of the following configurations are provided:
the auxiliary filter extends along the outer side of the conduit such that it overlaps the upstream opening but does not overlap the downstream opening;
the auxiliary filter extends along the outer side of the conduit such that it overlaps the downstream opening but does not overlap the upstream opening; and
the auxiliary filter extends along the outer side of the conduit such that it overlaps both the upstream opening and the downstream opening.

12. The bypass filter according to claim 9, wherein the auxiliary filter is fitted with a downstream cover configured to prevent water from dripping down after being absorbed within the auxiliary filter.

13. The bypass filter according to claim 12, wherein the downstream cover comprises one or more cover apertures configured to allow the gases to escape via a downstream end of the auxiliary filter.

14. The bypass filter according to claim 13, wherein the bypass filter comprises an external housing surrounding at least the auxiliary filter that fully encapsulates the bypass filter.

15. The bypass filter according to claim 14, wherein the auxiliary filter extends between an upstream end located upstream of the upstream opening of the conduit, and a downstream end located downstream of the downstream opening of the conduit.

16. The bypass filter according to claim 14, wherein the auxiliary filter is configured to increase in dimensions upon absorbing liquid.

17. The bypass filter according to claim 16, wherein the external housing comprises a stopper configured for limiting axial expansion of the auxiliary filter due to ab sorption of liquid.

18. The bypass filter according to claim 17, wherein once the auxiliary filter expands sufficiently to reach the stopper, the one or more cover apertures of the downstream cover become blocked, thereby preventing passage of gases to the downstream opening of the conduit.

19. The bypass filter according to claim 1, wherein the conduit wall defines a plurality of bypass apertures between the upstream opening and the downstream opening, each bypass aperture of the plurality of bypass apertures extending through the conduit wall, wherein the auxiliary filter is in fluid communication with at least one of the upstream opening or the downstream opening through at least the plurality of bypass apertures.

20. The bypass filter according to claim 1, wherein the conduit wall is impenetrable to the fluid.

* * * * *